US010206873B1

(12) United States Patent
Gildelamadrid et al.

(10) Patent No.: US 10,206,873 B1
(45) Date of Patent: Feb. 19, 2019

(54) DRY POWDER FORMATION USING A VARIABLY CONSTRAINED, DIVIDED PATHWAY FOR MIXING FLUID STREAMS

(71) Applicants: Xuno Gildelamadrid, Fort Morgan, CO (US); Robert E. Sievers, Boulder, CO (US)

(72) Inventors: Xuno Gildelamadrid, Fort Morgan, CO (US); Robert E. Sievers, Boulder, CO (US)

(73) Assignee: COLORADO CAN LLC, Boulder, CO (US)

( * ) Notice: Subject to any disclaimer, the term of this patent is extended or adjusted under 35 U.S.C. 154(b) by 0 days.

(21) Appl. No.: 15/669,118

(22) Filed: Aug. 4, 2017

(51) Int. Cl.
*A61K 9/00* (2006.01)
*A61K 38/28* (2006.01)
*B01F 3/00* (2006.01)
*B01J 2/04* (2006.01)

(52) U.S. Cl.
CPC ............ *A61K 9/0075* (2013.01); *A61K 38/28* (2013.01); *B01J 2/04* (2013.01); *A61M 2202/064* (2013.01); *B01F 2003/0064* (2013.01)

(58) Field of Classification Search
CPC ......... A61K 9/0075; A61K 38/28; B01J 2/04; B01F 2003/0064
See application file for complete search history.

(56) References Cited

U.S. PATENT DOCUMENTS 6,630,121 B1 * 10/2003 Sievers ................ A61K 9/1694 424/1.13
6,931,888 B2 8/2005 Shekunov et al.
7,175,886 B2 2/2007 Del Re et al.
7,250,152 B2 7/2007 Gentile et al.
7,279,181 B2 10/2007 Chattopadhyay et al.
7,332,111 B2 2/2008 Grothe et al.
7,378,110 B2 * 5/2008 Truong-Le ........... A61K 9/1694 424/489
7,449,136 B2 11/2008 Shekunov et al.
7,455,797 B2 11/2008 Shekunov et al.
7,635,442 B2 12/2009 Del Re et al.
7,798,475 B2 9/2010 Demirüker
8,167,279 B2 5/2012 Demirüker
8,609,611 B2 12/2013 Foster et al.
8,642,091 B2 2/2014 Shekunov et al.
2002/0189454 A1 12/2002 Perrut
2006/0105051 A1 5/2006 Jackson et al.

FOREIGN PATENT DOCUMENTS

WO 2010/009239 A2 1/2010

* cited by examiner

*Primary Examiner* — Mina Haghighatian
(74) *Attorney, Agent, or Firm* — Porter Wright Morris & Arthur LLP

(57) ABSTRACT

Methods of making a dry powder, comprise (a) delivering a liquid solution or suspension and a second, immiscible fluid to a flow path, (b) transporting the liquid solution or suspension and the immiscible fluid along the flow path, wherein the flow path includes two or more flow passages of different diameters, at least one flow divider which divides and diverts the flowing mixture into at least two separate passages, wherein the separate passages subsequently intersect to combine their respective flows into a single flowing stream, (c) rapidly reducing the pressure of the single flowing stream, whereby droplets are formed, and (d) passing the droplets through a flow of inert drying gas to form a dry powder. A nebulizing nozzle includes an inlet, a flow path as described, and a restrictor nozzle outlet.

21 Claims, 13 Drawing Sheets

DRY POWDER FORMATION USING A VARIABLY CONSTRAINED, DIVIDED PATHWAY FOR MIXING FLUID STREAMS

FIELD OF THE INVENTION

The present invention is directed to methods of making a dry powder by mixing a liquid solution or suspension and an immiscible supercritical or near critical fluid and transporting the liquid solution or suspension and the immiscible fluid through a defined flow path and a nebulizing nozzle. In the defined flow path, the liquid solution or suspension and the immiscible supercritical or near critical fluid are thoroughly mixed through a sequential variation in flow path diameter and a division and reunification of the flow path. A fine emulsion or solution exits the nozzle is dried under a stream of inert drying gas to produce a dry powder.

BACKGROUND OF THE INVENTION

Dry powder preparations are used ubiquitously throughout the pharmaceutical, nutraceutical, biotechnological and food industries. Particle engineering often incorporates elements from microbiology, chemistry, formulation science, colloid and interface science, heat and mass transfer, solid state physics, aerosol and powder science, and nanotechnology (Vehring 2007). Processing methods for the production of dry powders include spray drying, spray freeze drying, wet chemistry and phase separation processes, as well as supercritical fluid technologies.

Powder processing technologies are constantly being improved to in an attempt to satisfy increasing demands for more advanced particle engineering. Use of dry powders in specific fields such as respiratory drug delivery, for example, requires powder particles to be within a certain aerodynamic diameter range and possess excellent aerodynamic properties that enable their inspiration into the lungs instead of agglomerating and impacting on the back of the throat where they are retained. Additional characteristics such as rapid dissolution in aqueous lung fluid or through membranes into the blood and emulsification of hydrophobic drug molecules may also be beneficial attributes of an inhalable particle.

Initially, drying technologies served only as crude micronization and solvent-removal methods, and lacked versatility. During the last decade or so, efforts have been undertaken to more completely understand particle formation and control particle morphology. Particle morphology, described by such characteristics as size, shape, internal and exterior structure, and surface properties, is difficult to intentionally design using an empirical approach because of the sheer number of variables involved in the drying process (Vehring 2007). Numerous process variables, such as drying temperature, drying gas flow, nebulizer nozzle parameters, sample solvent, and collection method, are compounded by an almost infinite number of possible formulation components and combinations thereof. To mitigate this task, attempts are being made to derive mathematical equations, computer models, and representative experiments to approximate and predict the thermodynamics, kinetics, and chemical interactions that occur during the drying of a droplet in a spray dryer.

In the case of designing powders for respiratory drug delivery, a particle characteristic of particular importance is aerodynamic diameter, which is defined as the diameter of a unit-density sphere that has the same settling velocity as the measured particle (Vehring 2007). Aerodynamic diameter is useful for approximating the extent of entrainment of a particle in an airflow, and should not be confused with geometric diameter, which is the physical distance across the particle as determined by microscopy. Control of particle aerodynamic diameter during the spray drying process has been found to be partially described by the following equation (Vehring 2007):

$$d_a = \sqrt[6]{\frac{\rho_P}{\rho^*}}\sqrt[3]{\frac{c_F}{\rho^*}}\,d_D. \qquad \text{Equation 1}$$

where $d_a$ is aerodynamic diameter, $\rho_p$ is particle density, $\rho^*$ is the reference density of 1 g/cm$^3$, $C_F$ is the feed solution concentration, and $d_D$ is the droplet diameter. It can be seen from Equation 1 that the small aerodynamic diameter required for lung deposition of a particle (1-5 μm) can be controlled by lowering the spray dryer feed solution concentration, by making particles of low density, and/or by decreasing the droplet diameters formed by the spray dryer nozzle. Decreasing the feed solution concentration is often an unattractive option, particularly when scale-up efforts are considered, as it leads to lower product yields during a given timeframe. Achieving small aerodynamic diameters through decreased droplet size and decreased particle density is therefore a superior method for obtaining powders with respirable characteristics.

In addition to controlling the aerodynamic diameter of a particle by lowering its density, irregular surface morphologies can be engineered to maximize the interaction of the particle with an airflow. Pockets, crevices, pores, and other varied surface features allow improved entrainment of a particle in flowing air, imparting significantly improved aerodynamic properties for inspiration into the lungs.

Droplet diameter is largely a function of the performance of the spray dryer nozzle, although certain formulation components that have a large effect on solution properties can also play a role. There are four types of nozzles frequently encountered in spray drying: rotary atomizers, pressure nozzles, two-fluid nozzles (Masters 1972, Sacchetti 1996), and ultrasonic atomizers (Bittner 1999, Freitas 2004). An additional, less common, nozzle that utilizes near-critical or supercritical carbon dioxide will be described presently. Commonly, droplet mass median diameters (MMDs) in pharmaceutical spray dryers range from less than 10 μm to more than 100 μm, producing dried particles with corresponding geometric diameters of 0.5 μm to 50 μm (Vehring 2007).

In contrast to feed solution concentration and droplet diameter, which are dictated by yield requirements and spray dryer design, respectively, particle density has been predominantly controlled by judicious selection of the composition of the formulation. Typically, to obtain powder particles of low density, excipients are added to the feed solution that predispose the drying droplets to form particles that possess either "folded shell" or "solid foam" morphology. Such morphologies contain empty spaces, or voids, within the particle that impart a lower apparent or effective gross density to the particle than that of a solid sphere of identical geometric diameter. Low densities allow particles of larger geometric diameters, which possess superior handling properties such as reduced aggregation and increased dispersibility, to behave aerodynamically as smaller particles that are suitable for respiration into the lungs. Production of very low density particles is therefore desirable and is the focus of current research within the respirable drug delivery field.

Drying of a droplet into a particle with folded-shell morphology is schematically depicted in FIG. 1 (Vehring 2007). Incorporation of formulation excipients that have high Peclet numbers (low mobility within the droplet) causes selective enrichment of that excipient at the surface of the droplet as its boundary recedes during drying. As solvent is progressively removed from the droplet, a shell begins to form at the droplet surface that impedes further reductions in size of the outer diameter. Further solvent evaporation then occurs from near the center of the droplet, causing structural instability that results in buckling of the sphere or complete crumpling.

Excipients that have high Peclet numbers, such as proteins and polymers, are commonly encountered in pharmaceutical powder formulations. Various hollow, dimpled, or wrinkled particle morphologies resulting from the folding-shell drying pathway have been achieved with protein (Vehring, Foss 2007, Maa 1997, Maury 2005, Chew 2001, Maa 1998, Ameri 2006, Samborska 2005), peptide (Zijlstra 2004, Stahl 2002), and polymer (Bittner 1999, Wang 1999, Ting 1992, Baras 2000, Li 2006, Bernstein 1997, Mu 2001, Fu 2001) additives (Vehring 2007). The archetypal shell-forming excipient, leucine, is an excellent shell-former due to its low solubility in aqueous and alcoholic solutions (Vehring 2007), which causes it to reach saturation, precipitation, and a resulting high Peclet number early in the droplet drying process. Because of this, as well as its weak surfactant properties, leucine has been widely used in the spray drying industry to improve flowability and dispersibility of powders (Li 2006, Begat 2005). An example of the change in morphology that can be accomplished with the addition of leucine to a powder formulation is depicted in FIG. 2 (Vehring 2007). Spray-dried immunoglobulin particles form a buckled, folded-shell morphology when the protein is dried alone, as the immunoglobulin protein itself has a high Peclet number (FIG. 2A). However, when leucine is added to the formulation, the particles adopt a wrinkled surface in addition to the buckled, folded shell (FIG. 2B).

Like particles with folded-shell morphologies, particles of solid foam compositions can also possess very low densities due to the presence of internal and/or external voids. However, unlike the process of creating folded shells, spray drying solid foam particles does not rely on excipients with high Peclet numbers. Instead, formulations are designed that incorporate one or more "blowing agents," volatile additives with high boiling points that serve as "place-holders" within the drying droplet. The blowing agent remains distributed throughout the droplet during drying, and is evaporated or sublimed after most of the droplet drying is complete or during a separate, secondary drying event. Removal of the blowing agent after the particle is dry results in the creation of pores of empty space as the blowing agent evolves from the dried particle matrix. Blowing agents may be volatile salts that sublime upon heating, such as ammonium bicarbonate (Straub 2003) or ammonium carbonate (Narayan 2001), or alternatively, volatile oils. An exemplary case in which a volatile oil has been used to create solid foam particles is PulmoSpheres™, depicted in FIG. 3 (Vehring 2007). PulmoSpheres™ are created from the eventual evaporation of perflubron, a volatile oil that is incorporated into the formulation via an emulsion formed prior to spray drying (Geller 2011).

Although incorporation of certain excipients into the formulation can dispose the droplet drying process to form particles of low density, in many cases it is impractical or undesirable to allow the composition of the powder to be dictated by the necessary inclusion of these additives. In many cases, such as that for the shell-former leucine, the excipient must be included in the formulation in relatively large quantities. For example, in the immunoglobulin example previously noted, it was necessary to incorporate leucine into the particles at 25% of the total weight in order to achieve the desired change in morphology (Vehring 2007). The delivery of immunoglobulin, the active ingredient, would therefore be diminished by a quarter in order to achieve a powder with an improved respirable fraction as compared to pure protein particles. Sacrifices of drug concentration within a particle for the sake of improved aerodynamic properties may be untenable in many situations. Additionally, in the case of respirable drug delivery, each additional excipient must be thoroughly tested for toxicity when inhaled into the lungs, an expensive and time-consuming process.

In addition to contributing to the dilution of active ingredients, the presence of additives that are necessary to obtain desired respirable fractions may be detrimental to the storage stability of the powder. To be physically stable, particles should be created in either a fully crystalline state, or as an amorphous glass with a high glass transition temperature and high viscosity. Particles composed of mixed states, such as partially crystalline or a mixture of polymorphs, exhibit reduced stability due to spontaneous nucleation and growth of the more stable crystalline polymorph. Crystallization during storage of amorphous fractions of a particle often leads to water expulsion and plasticization of the powder (Vehring 2007). Potential incompatibilities among neighboring physical states within the particle increase as the complexity of the formulation increases: the potential for components that spray-dry in crystalline form to negatively impact other components that spray-dry in an amorphous form is higher when the number of additives is large. Likewise, the chemical stability of a particle is partly dependent on any possible reactions among the ingredients, and the potential for a reaction increases with the number of formulation components.

The drawbacks of a complex, multi-excipient formulation can be eliminated if the ideal low-density particles can be created inherently by a novel spray-drying technology itself. Engineering the process to create hollow particles through the physical introduction of voids, irrespective of the formulation, will be of great benefit to the industry, particularly in the field of respiratory drug delivery. Promising methods for the achievement of this goal include the use of supercritical fluid (SCF) technology in the design of new nozzles, with the aim of affecting the atomization of the feed solution stream such that the drying of bubbles, instead of solid droplets, is accomplished. Previous work is schematically represented in FIG. 4 and described in U.S. Pat. No. 6,630,121, incorporated herein by reference in its entirety, in which a Carbon Dioxide-Assisted Nebulization with a Bubble Dryer (CAN-BD) nozzle is employed to mix near-critical carbon dioxide with the feed solution in a low-volume tee. The mixture travels down a 75 μm restrictor and quickly expands to atmospheric pressure in a drying chamber, forming a combination of bubbles and solid droplets. In the drying chamber, dry, warm gas (usually nitrogen) removes the solvent from the bubbles and droplets, and the dried particles are collected on an inline filter to be removed from the gas flow (Sellers 2001). This method has been shown to form a combination of hollow and solid particles (in the absence of shell-forming excipients or blowing agents) with the distribution strongly in favor of solid particles, as illustrated in FIG. 5 (Cape 2008).

However, the use of carbon-dioxide as the nebulizing gas within the nozzle allows for the production of particles with smaller average geometric diameters than the same nozzle configuration with nitrogen as the nebulizing gas, as illustrated in FIG. 6. Nitrogen or air as a nebulizing gas is commonly used in traditional spray dryer nozzles. The small geometric diameters of CAN-BD-produced particles produced by a process in which the carbon dioxide is substituted for nitrogen as the drying gas often translate into small aerodynamic diameters, as predicted by Equation 1, if suitable formulation components are incorporated to enhance dispersibility and hollow particle formation. The CAN-BD process therefore represents an advancement toward the engineering of respirable particles through the precise control of droplet size to create small geometric diameters; however, the process is highly reliant on formulation composition to achieve small particle aerodynamic diameters and dispersible powders. Improvements to the CAN-BD process that allow for the creation of hollow particles, and thus small aerodynamic diameters, irrespective of, will be of great benefit.

SUMMARY OF INVENTION

It is therefore an object of the invention to provide a method for making dry powder and to provide dry powder having relatively low-density particles, irrespective of the chemical composition of the particles. It is a further object of the invention, in certain embodiments, to provide a method for making dry powder comprising low-density particles having aerodynamic properties suitable for inhalation, irrespective of the chemical composition of the particles.

In one embodiment, the invention is directed to the incorporation of an improved nozzle into a spray dryer. The improved nozzle comprises a variably constrained, divided pathway in which a liquid solution or suspension containing at least one solute or suspended component and an immiscible supercritical or near critical fluid are thoroughly mixed to form a fine emulsion or suspension. The emulsion or suspension is released and then subjected to drying in a flowing stream of gas after leaving the nozzle. The dry powder thus formed comprises particles of relatively low density.

In yet another embodiment, the invention is directed to a method of providing a respirable fraction of a dry powder for inhalation into the lungs irrespective of the chemical composition of the particles. The method comprises the mixing of at least one liquid solution or suspension which contains a solute or solid to be dried, and supercritical or near critical carbon dioxide through a variably constrained, divided pathway into a fine emulsion. The emulsion is then subjected to drying in a flowing stream of gas. The dry powder thus formed has aerodynamic properties suitable for respiration into the lungs.

In another embodiment, the invention is directed to a method of making a dry powder. The method comprises (a) delivering a liquid solution or suspension and an immiscible supercritical or near critical fluid to a flow path, (b) transporting the liquid solution or suspension and the immiscible fluid along the flow path, wherein the flow path includes two or more flow passages of different diameters, at least one flow divider which divides and diverts the flowing mixture into at least two separate passages, wherein the separate passages subsequently intersect to combine their respective flows into a single flowing stream, (c) rapidly reducing the pressure of the single flowing stream, whereby droplets are formed, and (d) passing the droplets through a flow of inert drying gas to form a dry powder.

In yet another embodiment, the invention is directed to a nebulizing nozzle comprising at least one inlet, a restrictor nozzle outlet, and a flow path in communication with the inlet and the restrictor nozzle outlet, wherein the flow path includes a first passage in communication with the inlet and having a first diameter, followed by a second passage having a second diameter larger than the first diameter, followed by a third passage having a third diameter smaller than the second diameter, followed by a flow divider which divides and diverts flow into at least two separate passages, wherein the separate passages subsequently intersect to combine and form a fourth passage in communication with the restrictor nozzle outlet.

The methods according to the invention are advantageous in creating particles of low density irrespective of the chemical composition of the particles. In certain embodiments, the dry powders according to the invention are advantageous in comprising particles of morphologies and aerodynamic properties suitable for inhalation into the lungs. These and additional advantages of the invention will be more evident in view of the following detailed description of the invention.

BRIEF DESCRIPTION OF DRAWINGS

The detailed description of the invention will be more fully understood in view of the drawings, in which.

Figure 1:
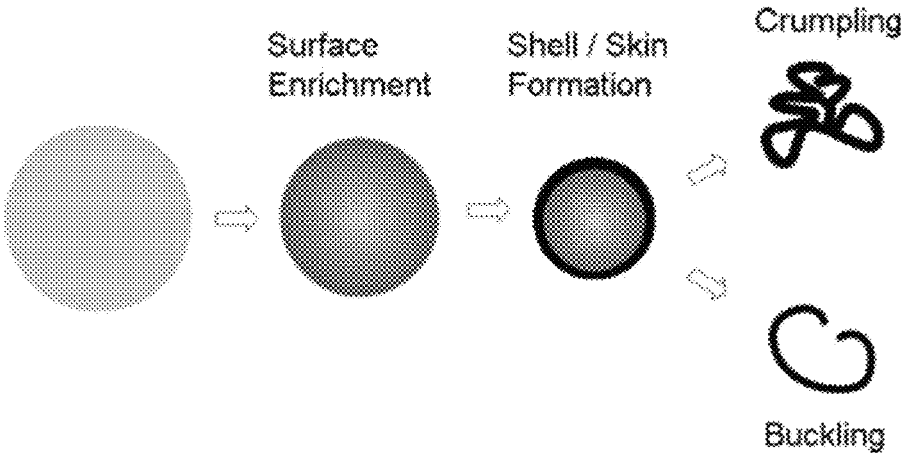
FIG. 1 shows a schematic diagram of the formulation-dependent drying process of a droplet into a particle with folded-shell morphology (Vehring 2007).
Figure 2A:
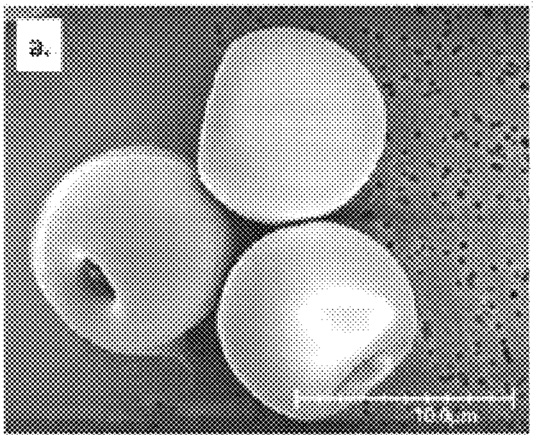
FIG. 2A shows the morphology of folded-shell immunoglobulin particles spray dried without the addition of leucine (Vehring 2007) and FIG. 2B shows the morphology of folded-shell immunoglobulin particles spray dried with the addition of 25% leucine by weight (Vehring 2007).
Figure 2B:
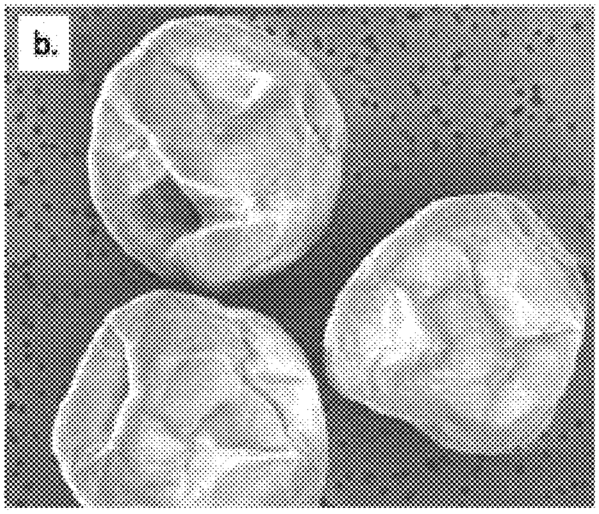
Figure 3:
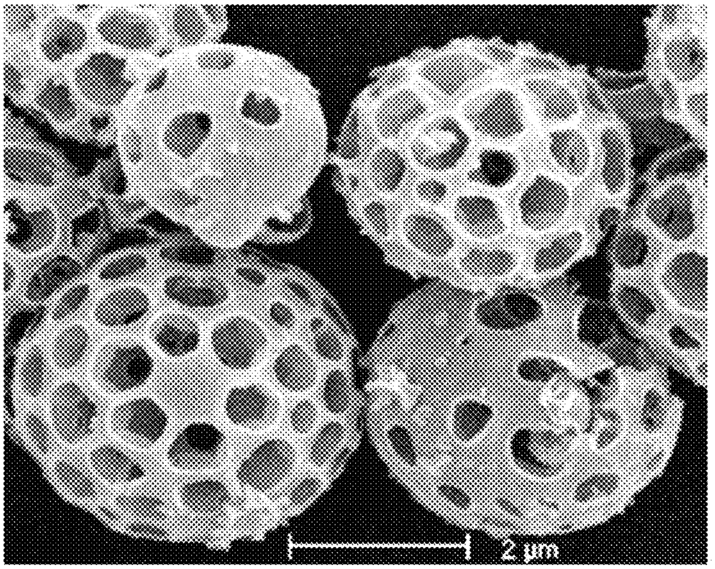
FIG. 3 shows the morphology of a solid-foam particle created under the trade name of PulmoSpheres™ (Vehring 2007).

The drawings show certain features related to the invention but are not to be construed as limiting of the invention in any manner.

DETAILED DESCRIPTION

The present invention provides a method for the creation of relatively low-density particles irrespective of the chemical composition of the particles and, in certain embodiments, provides a method for the creation of low-density particles of aerodynamic properties suitable for inhalation, irrespective of the chemical composition of the particles.

In order to obviate the need for shell-forming excipients or blowing agents in the creation of low-density particles, voids must be created within the particle physically during the spray-drying process. Immiscible supercritical or near critical fluids such as supercritical carbon dioxide or near critical carbon dioxide are improved nebulizing mediums for the creation of gas-filled bubbles. After leaving the nozzle, the bubbles may be dried quickly under a stream of warm, dry gas to produce hollow particles.

In contrast to the mechanism of traditional spray dryer nozzles, in which the forceful aerosolization of droplets is accomplished only by the proximity of the feed solution to a stream of a pressurized gas, the formation of gas-filled bubbles necessitates that the nebulizing gas and liquid solution become intimately mixed prior to exiting the nozzle. Carbon dioxide is preferred over many other fluids in this respect as it is easily compressed at room temperature into a liquid at reasonable pressures (above 900 psig). In its fluid state, carbon dioxide assumes the physical properties associated with liquids, and can be intimately mixed into an emulsion with another liquid. The cellular structure of the emulsion forms the basis for a fine plume of droplets to be created once the emulsion is rapidly decompressed to atmospheric pressure. Small particles are created by the greater expansion ratio, and thus greater expansion energy, of the liquid carbon dioxide than that of gaseous nitrogen. The volume expansion ratio of liquid carbon dioxide is roughly 1:533 (liquid:gas), while the expansion of gaseous nitrogen will simply follow the linear relationship defined by the ideal gas law. Rapid release of pressurized liquid carbon dioxide to atmospheric pressure produces greater energy release and greater atomization of the droplets in the spray plume, ultimately resulting in dried particles of smaller average geometric diameters than the same nozzle conditions with compressed nitrogen as the nebulizing gas.

Additionally, carbon dioxide has a much higher solubility in water (about 80-fold) at room temperature than does nitrogen. The higher solubility of carbon dioxide and the solvent properties, controlled by pressure, of its liquid phase allow for the dissolution of some of the carbon dioxide in the liquids with which it is mixed. According to Henry's law, the solubility of gases in liquids increases proportionately with increasing pressure, allowing a substantial amount of carbon dioxide to be dissolved in the opposing liquid upon mixing. The dissolved carbon dioxide serves as a placeholder within a droplet after leaving the nozzle, and upon return to atmospheric pressure, much of the dissolved carbon dioxide leaves the droplet as a gas, creating hollow regions within the particle. The timescale of the oversaturation, followed by vaporization and removal from the droplet, of the dissolved carbon dioxide is slower than the vaporization of the liquid carbon dioxide contained in the emulsion. Through the combination of these processes, small droplet diameters are created, and hollow regions within the droplets are formed, resulting in the creation of small, low-density particles. To accomplish this, the emulsion and dissolution of carbon dioxide within the mixing space must be as thorough and consistent as possible, and the liquids must be allowed to mix completely.

Figure 7:
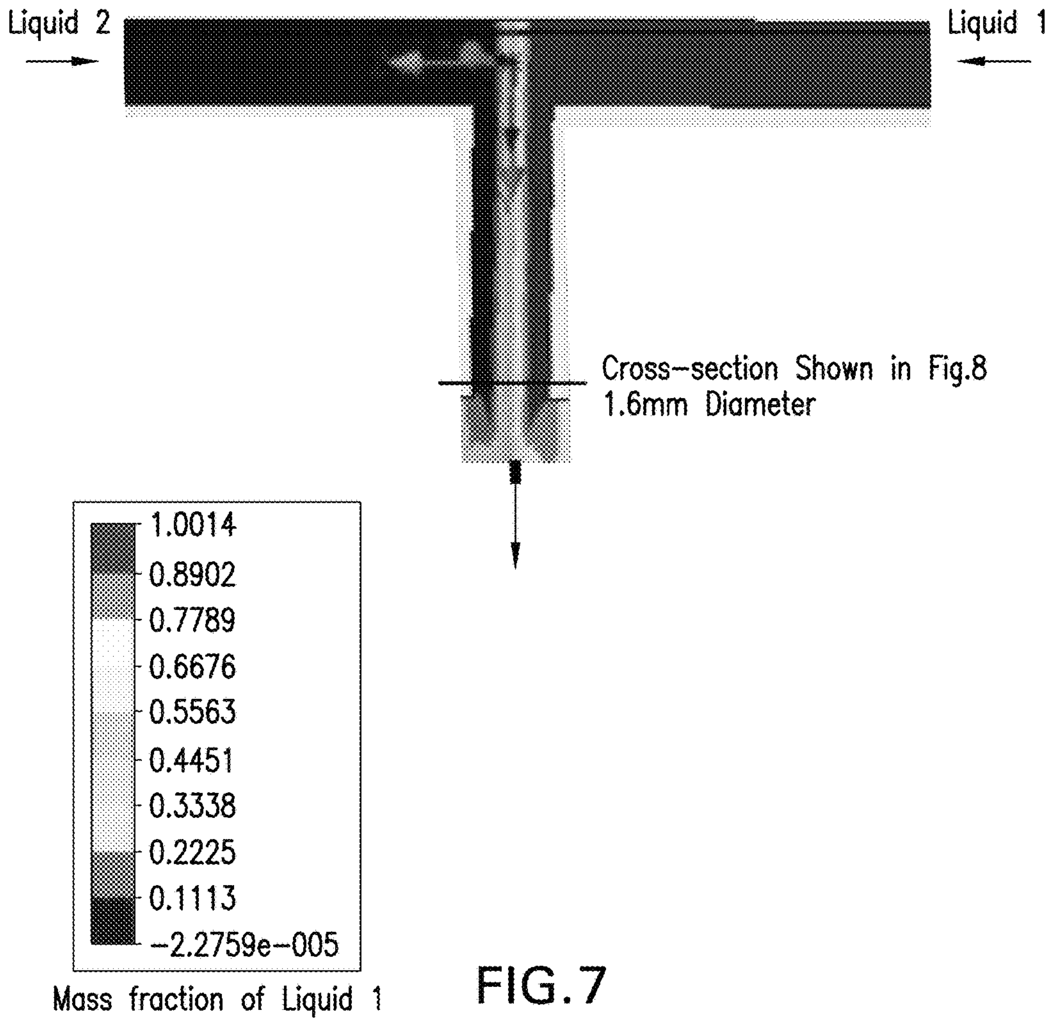
FIG. 7 shows a schematic diagram of the flow pattern and mixing of two liquids inside the CAN-BD nozzle described in U.S. Pat. No. 6,630,121, as modelled by the computational fluid dynamics (CFD) capability of Solidworks® software.
Figure 8:
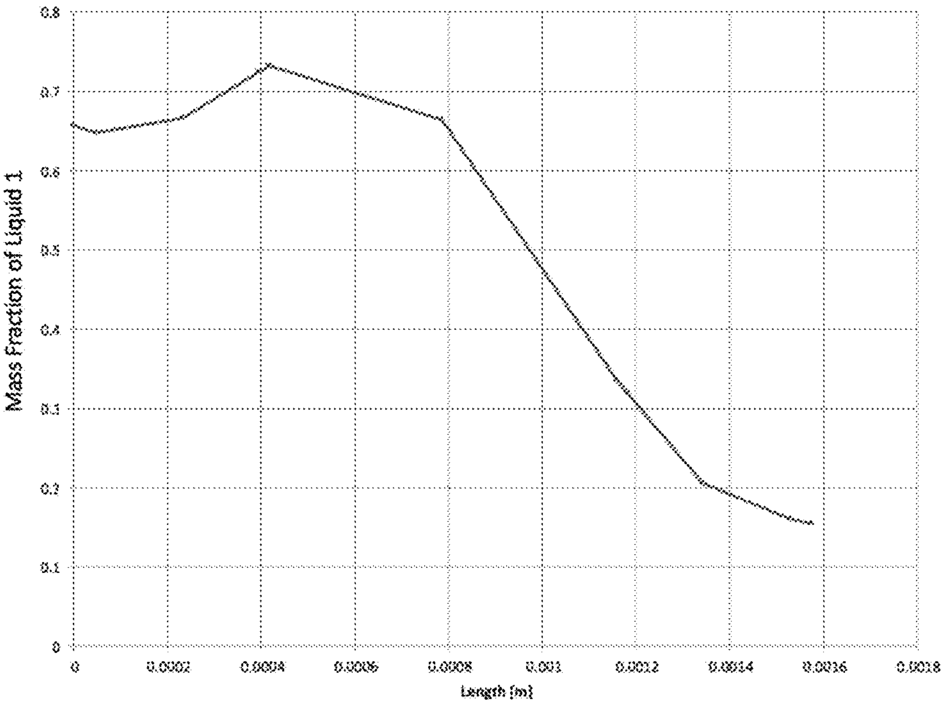
FIG. 8 shows quantitatively the extent of mixing of two liquids inside the CAN-BD nozzle described in U.S. Pat. No. 6,630,121, as modelled by the CFD capability of Solidworks® software and represented by the mass fraction of one of the liquids encountered across a lateral cross section of the opening of the tee.

Accordingly, incomplete mixing of the fluid carbon dioxide and liquid solution is likely to result in only a portion of the resultant particles possessing a hollow morphology. The mixing of equal proportions of two liquids inside the current CAN-BD nozzle described by U.S. Pat. No. 6,630,121, as modelled by Solidworks® using computational fluid dynamics (CFD), is schematically depicted in FIG. 7. In this configuration, partial mixing of the two liquids occurs at the boundary between them (indicated in light grey), but a substantial portion of each liquid remains in an unmixed form. The extent of mixing of the two liquids is shown quantitatively in FIG. 8, which shows the mass fraction of one of the liquids across a lateral cross-section of the outlet in the tee. Absolute mixing would be represented by a flat line at 0.5 mass fraction across the entire lateral cross section.

Figure 9:
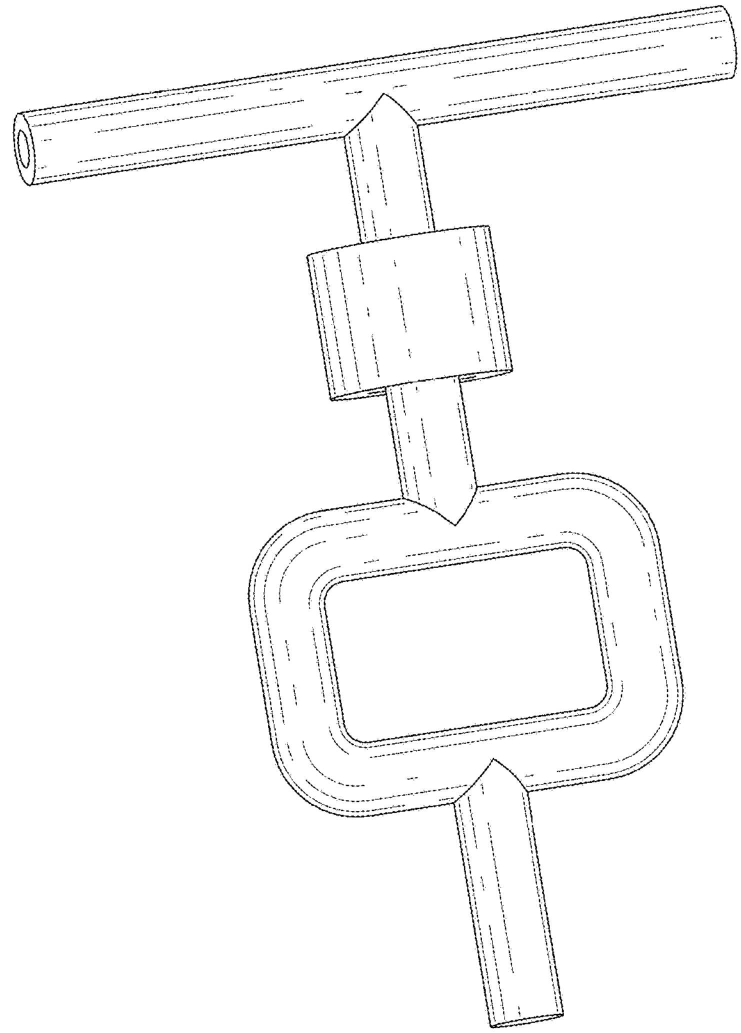
FIG. 9 shows a 3D model of an example nozzle of the invention as described in Example 1, rendered by Solidworks® software.

Mixing is improved immensely according to the invention when a variably constrained (variable diameter), divided pathway is introduced into the nozzle in place of the simple meeting of two liquid streams which is described in U.S. Pat. No. 6,630,121. One embodiment of a nozzle for use in the present invention is shown schematically in FIG. 9. By variably constraining and dividing the flow pathway, turbulence, eddies and other flow perturbations are introduced that encourage mixing of the two liquids. Initially, the nozzle invention comprises a similar geometry to the low-volume tee described in U.S. Pat. No. 6,630,121. The two liquid streams meet in the center of the tee, in which partial mixing takes place.

The flow then progresses through an area of variable constraint, such that the diameter of the flow path is variable, i.e., increased and decreased along the flow path. In a specific embodiment, the flow path is initially increased and then decreased. In an alternate specific embodiment, the flow path is initially decreased and then increased. The variation in constraint may encompass any suitable effective pathway diameter for a desired amount of liquid mixing. Within the present disclosure, reference to a flow path passage diameter refers to the inside diameter of a conduit constituting the flow path passage. In a specific embodiment, the diameter along the flow path is constrained, i.e., may vary, from about 0.01 mm to about 8 mm. In a more specific embodiment, the diameter is constrained from about 2 mm to about 7 mm. In yet a more specific embodiment, the diameter is constrained from about 1.5 mm to about 6 mm. Additionally, the diameter may be constrained in a manner as to produce particles suitable for inhalation. Suitable diameters along the flow path include from about 0.01 mm to about 8 mm, more specifically from about 2 mm to about 7 mm, and even more specifically from about 1.5 mm to about 6 mm. These dimensions are exemplary only and various components of the nozzle may occur in any order, in any number of repetition, and at any distance between the meeting of the supercritical fluid and feed solution or suspension and the restrictor nozzle outlet.

The flow through the improved nozzle also progresses to an area of flow pathway division, such that the flow stream is divided into two or more branches or separate passages. The number of divisions may encompass any suitable effective number for a desired amount of liquid mixing. In a specific embodiment, the number of branches comprises from about 2 to about 4. In a more specific embodiment, the number of branches comprises from 2 or 3. In yet a more specific embodiment, the number of branches is 2. Additionally, the number of branches may be comprised in a manner as to produce particles suitable for inhalation. In specific embodiments, the separate passages have respective segments that are parallel to one another.

Figure 10A:
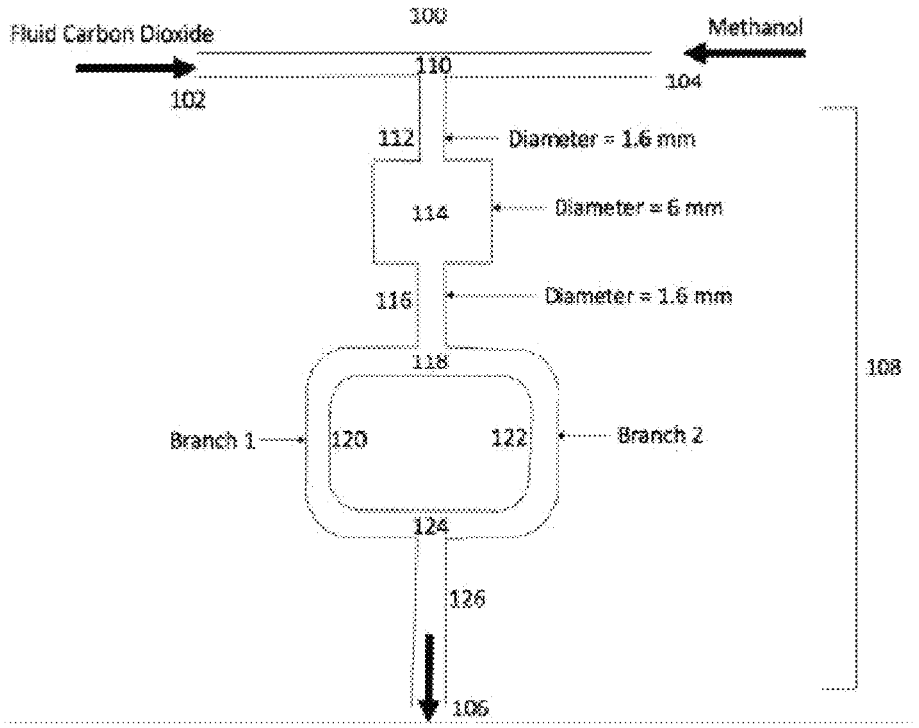
FIG. 10A shows a schematic diagram of a specific embodiment of a nebulizing nozzle according to the invention.

In a specific embodiment as shown in FIG. 10A, the invention is directed to a nebulizing nozzle 100 comprising at least one inlet, shown in FIG. 10A as inlets 102 and 104, a restrictor nozzle outlet 106, and a flow path 108 in communication with the inlet and the restrictor nozzle outlet. In the specific embodiment of FIG. 10A, the flow path includes a mixing T 110, followed by a first passage 112 in communication with the inlets and having a first diameter, followed by a second passage 114 having a second diameter larger than the first diameter, followed by a third passage 116 having a third diameter smaller than the second diameter, followed by a flow divider 118 which divides and diverts flow into at least two separate passages. In a specific embodiment, the separate passages have segments 120 and 122, respectively, which are parallel with one another. The separate passages subsequently intersect at 124 to combine and form a fourth passage 126 in communication with the restrictor nozzle outlet 106. This configuration is exemplary only and various components of the nozzle may occur in any order, in any number of repetition, and at any distance between the meeting of the supercritical fluid and feed solution or suspension and the restrictor nozzle outlet.

In more specific embodiments of the nebulizing nozzle shown in FIG. 10A, the first diameter is in a range of from about 0.1 to about 3.0 mm, the second diameter is from about 0.01 to about 8 mm greater than the first diameter, and the third diameter is about 0.01 to about 8 mm less than the second diameter. In further embodiments, the respective separate passages have diameters greater than the third diameter. In another embodiment, the fourth passage has a fourth diameter less than the diameters of the respective separate passages. In further embodiments, the first diameter is in a range of from about 0.1 to about 3.0 mm, the second diameter is in a range of from about 1.0 to about 6 mm, the third diameter is in a range of from about 0.1 to about 3.0 mm, the respective separate passages have diameters in a range of from about 1.0 to about 3.0 mm, the fourth diameter is in a range of from about 0.1 to about 3.0 mm, and the restrictor nozzle has a diameter of less than about 0.1 mm.

The length of the flow path over which each diameter is changed from one passage to the next is sufficiently short to achieve good mixing. In one embodiment, there is an abrupt change from one diameter to the next, with no transition area, as shown in FIG. 10A. In another embodiment, the length of the flow path over which each diameter is changed from one passage to the next ranges up to about the larger diameter of the two passages, up to about 0.5 times the larger diameter of the two passages, or up to about 0.25 times the larger diameter of the two passages.

The length of each passage of a constant diameter may be varied as desired. In a specific embodiment, the length of each passage of a constant diameter, i.e., each of the first through fourth passages, is of a length of at least the respective diameter of the passage.

The mass fraction of one liquid component in the mixture, upon complete mixing, will be substantially consistent throughout the entire lateral cross section of the opening of the nozzle and will be numerically defined by Equation 2:

$$w_i = \frac{Q_l}{Q_T}. \qquad \text{Equation 2}$$

where $w_i$ is the mass fraction of the liquid, $Q_l$ is the volumetric flow rate of the liquid, and $Q_T$ is the total volumetric flow rate. In a specific embodiment, the mass fraction of the liquid does not vary by more than about 25%, more than about 20%, more than about 15%, or more than about 10% throughout the entire lateral cross section of the opening of the nozzle. In a specific embodiment, the mass fraction of the liquid solution or suspension comprises from about 5 to about 95% of the mixture. In a more specific embodiment, the mass fraction of the liquid solution or suspension comprises from about 30 to about 80% of the mixture. In yet a more specific embodiment, the mass fraction of the liquid solution or suspension comprises from about 40 to about 70% of the mixture. The mass fraction of solute or suspended component in the liquid may vary widely. In a specific embodiment, the mass fraction of solutes and suspended components in the liquid is in a range of about 0.0001 to about 20%, to about 10%, to about 1% or to about 0.5%. Additionally, the composition of the mixture may be comprised as to produce particles suitable for inhalation. Suitable mass fractions of supercritical or near critical fluid, for example, liquid carbon dioxide, include from about 5% to about 95% of the mixture, more specifically from about 20% to about 70% of the mixture, and even more specifically from about 30% to about 60% of the mixture.

The liquid solution or suspension may have any desired composition based on the dry powder to be formed by the inventive methods and nozzle. In specific embodiments, the liquid comprises water, an organic solvent-water mixture, or one or more organic solvents. A liquid is easily selected depending on the composition of the component which is desired to be provided in dry powder form. In a specific embodiment, the liquid comprises water, an alcohol, more specifically, methanol, ethanol, isopropanol, propanol, a butyl alcohol, etc., or a mixture thereof. The solute or suspended material may comprise an active agent, examples of which include, but are not limited to, vaccines, insulin, amino acids, peptides, proteins, enzymes, anti-virals, anti-fungals, antibiotics, anti-inflammatory agents, antihistamines, analgesics, anti-cancer agents, antimicrobial agents, immune suppressants, thrombolytics, anticoagulants, central nervous system stimulants, decongestants, diuretic vasodilators, antipsychotics, neurotransmitters, sedatives, hormones, anesthetics, and siRNA. The liquid solution or suspension may further include one or more excipients selected from stabilizers, bulking agents, surfactants, anti-oxidants, and the like.

In a specific embodiment, the liquid solution or suspension includes a cannabinoid, a polymer binding agent, a dispersing agent, and a bulking agent, and, optionally, an antioxidant, as described in the Sievers et al U.S. application Ser. No. 15/466,719, filed Mar. 22, 2017, the disclosure of which is incorporated herein by reference in its entirety. Suitable polymer binding agents include polyvinylpyrrolidone (PVP), polyethylene glycol (PEG), poly(lactic-co-glycolic) acid (PLGA), polyvinyl alcohol (PVA), polyacrylic acid (PAA), N-(2-hydroxypropyl) methacrylamide (HPMA), polyoxazoline, polyphosphazenes, xanthan gum, gum arabic, pectins, chitosan derivatives, dextrans, carrageenan, guar gum, cellulose ethers, hyaluronic acid, albumin, and starch. Suitable dispersing agents comprise amino acids which act as surfactants, including methionine, alanine, arginine, asparagine, aspartic acid, cysteine, glutamic acid, glutamine, glycine, histidine, isoleucine, leucine, lysine, phenylalanine, proline, serine, threonine, tryptophan, tyrosine, valine, dipalmitoylphosphatidycholine (DPPC), phosphatidic acid (PA), phosphatidylethanolamine (PE), phosphatidylcholine (PC), phosphatidylserine (PS), phosphatidylglycerol (PG), Tween 20, and Tween 80. Suitable bulking agents comprise a non-hygroscopic polyol such as mannitol, gum Arabic, monosaccharides such as glucose, galactose, fructose, mannose, allose, altrose, fucose, gulose, sorbose, tagatose, arabinose, lyxose, rhamnose, ribose, xylose, erythrose, and threose, disaccharides such as lactose, maltose, sucrose, trehalose, lactulose, cellobiose, chitobiose, allolactose, sucralose, and mannobiose, and polyols such as maltitol, sorbitol, xylitol, erythritol, isomalt, arabitol, ribitol, galactitol, fucitol, iditol, myo-inositol, volemitol, lactitol, maltotriitol, maltotetraitol, maltodextrin, and polyglycitol. Suitable antioxidants include, but are not limited to, include vitamin A, vitamin C, vitamin E, alpha-carotene, astaxanthin, beta-carotene, canthaxanthin, lutein, lycopene, zeaxanthin, flavonoids (such as apigenin, myricetin, eriodictyol, theaflavin, genistein, resveratrol, malvidin), cinnamic acid, chicoric acid, chlorogenic acid, rosmarinic acid, curcumin, xanthones, eugenol, citric acid, oxalic acid, and lipoic acid. In a specific embodiment, the dispersing agent comprises methionine and an additional antioxidant is not employed.

In specific embodiments of the dry powder produced by the nozzle of the invention, at least 30% of particles have an aerodynamic diameter of less than 5.8 μm as modeled by an Andersen Cascade Impactor according to US Pharmacopeia <601>, and are thus suitable for respiration. Such powders will be effectively aerosolized by any dry powder inhaler and deposited in the airways. Low-density, easily-aerosolized powders may possess tap densities of 0.01 g/ml to 1 g/ml.

The particle distribution of the dry powder according to the invention comprises mixture of solid spheres and, importantly, hollow spheres. Specifically, the dry powder contains significantly more hollow spheres as compared to the typical CAN-BD nozzle-prepared powder which does not employ the variable flow path of the invention. In specific embodiments, the dry powder produced according to the invention comprises at least about 20%, at least about 25%, or at least about 30%, hollow spheres.

Various aspects of the dry powders and methods of the invention are illustrated in the following Examples.

Example 1

Mixing of equal volumes of two liquids according to the invention as described herein was modelled by CFD using the Solidworks® software.

The simulated liquid was methanol and the simulated immiscible fluid was supercritical or near critical carbon dioxide. The parameters were as follows: a first inlet was simulated to flow $1.5\times10^{-5}$ $m^3/s$ of methanol at a uniform flow rate. A second inlet was simulated to flow $1.5\times10^{-5}$ $m^3/s$ of liquid carbon dioxide at a uniform flow rate. The outlet was set to conditions of 101325 Pa and 293.2 K.

Figure 10B:
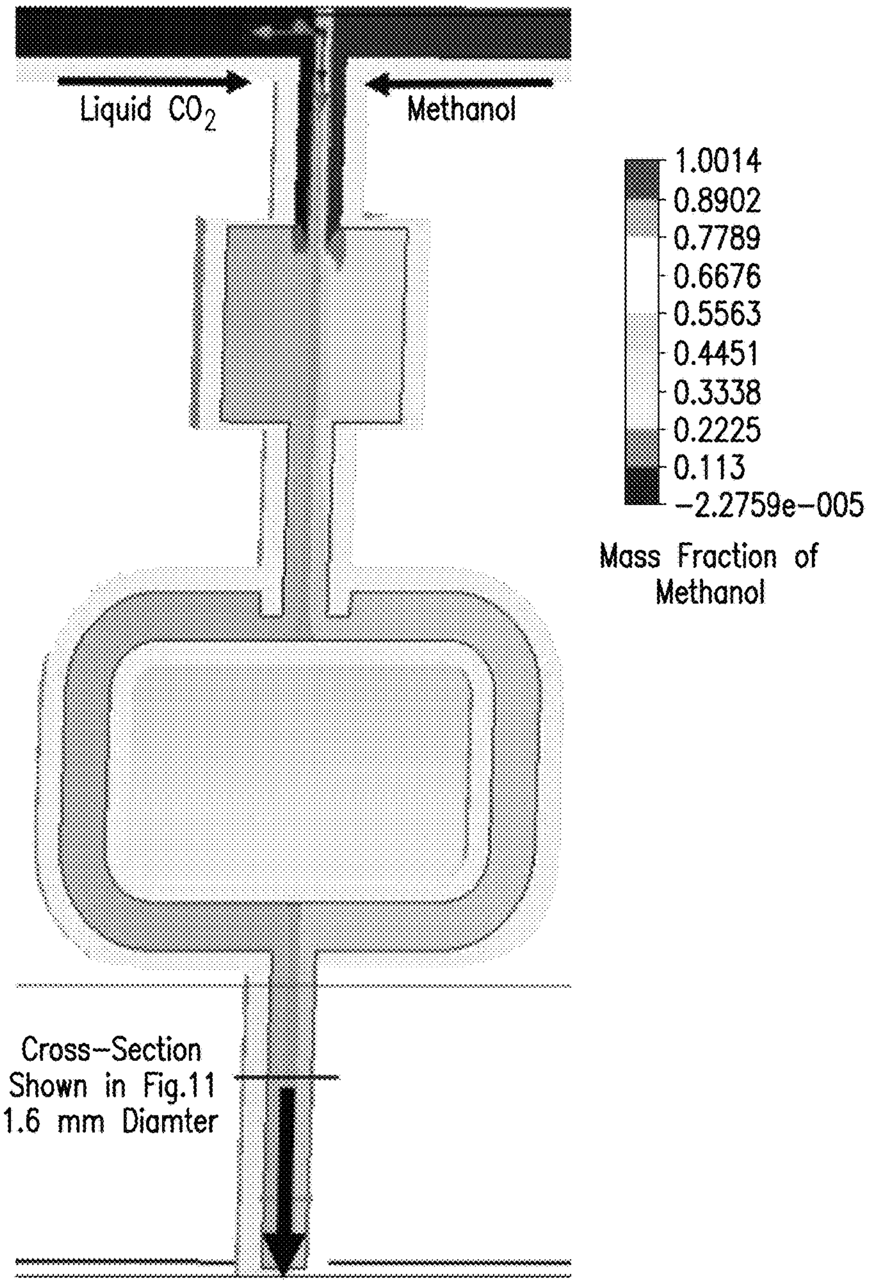
FIG. 10B shows a schematic diagram of the flow pattern and increased mixing of two liquids inside the nozzle of the invention, as modelled by the CFD capability of Solidworks® software and described in Example 1.
Figure 11:
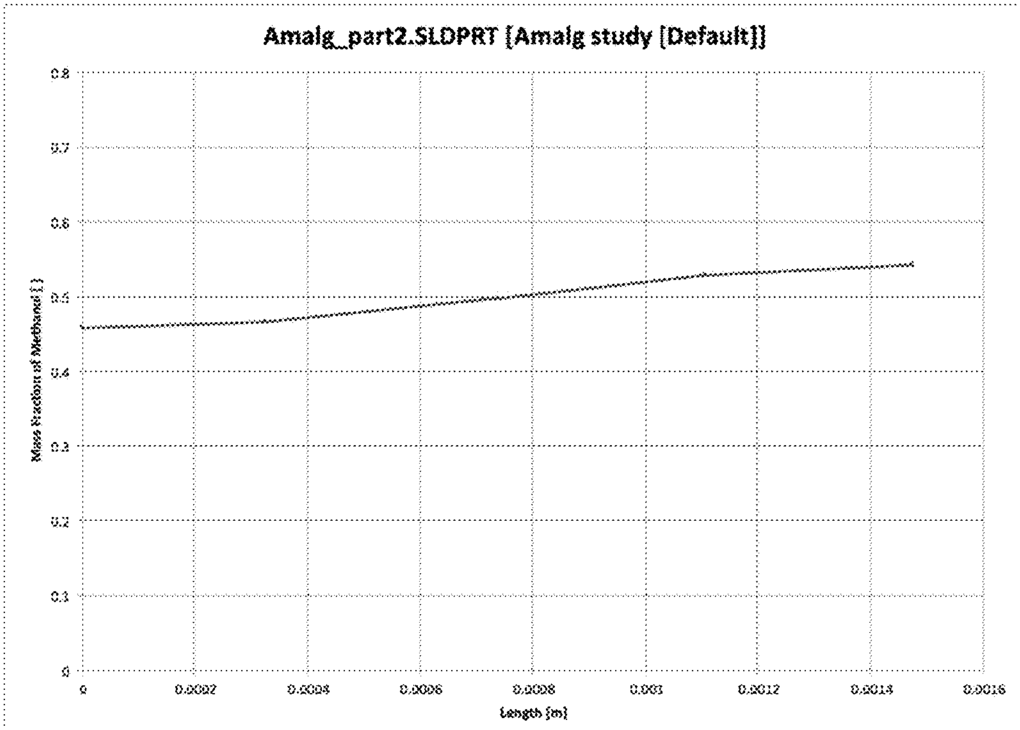
FIG. 11 shows quantitatively the extent of mixing of two liquids inside the nozzle of the invention, as modelled by the CFD capability of Solidworks® software and described in Example 1.

The results of the simulation are depicted schematically in FIG. 10B. The two streams (dark grey) were mixed nearly completely (mid-scale grey) by the time the flow stream reached the opening of the nozzle. The quantitative results of the simulation are shown in FIG. 11. The mass fraction of methanol approaches a value of 0.5 throughout the entire expanse of the lateral cross section of the nozzle opening, demonstrating thorough mixing of the two liquids.

Example 2

Dry inhalable powder according to the invention was prepared as described herein.

Figure 4:
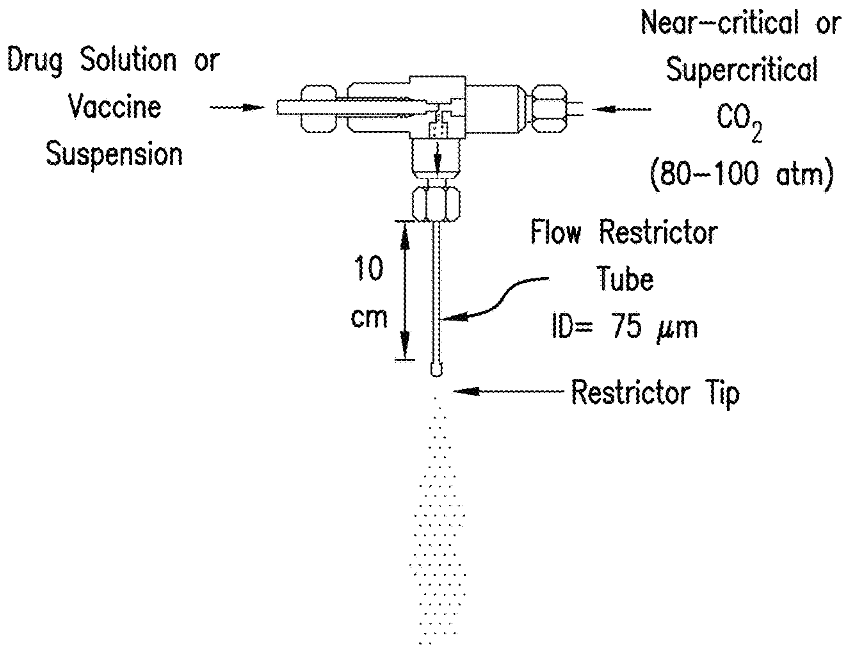
FIG. 4 shows a schematic diagram of the currently used CAN-BD nozzle described in U.S. Pat. No. 6,630,121.
Figure 5:
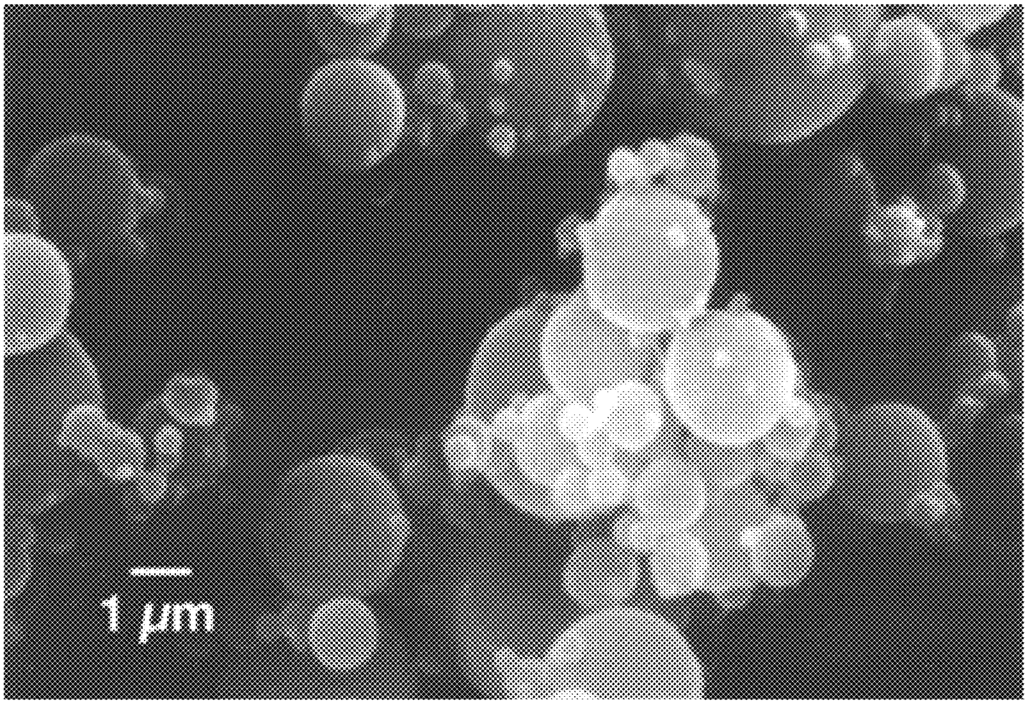
FIG. 5 shows a scanning electron micrograph (SEM) image of a typical CAN-BD-produced powder (produced from an aqueous solution containing 5% w/w sucrose) in the case in which no shell-forming or blowing agents are added to the formulation (Cape 2008).
Figure 6:
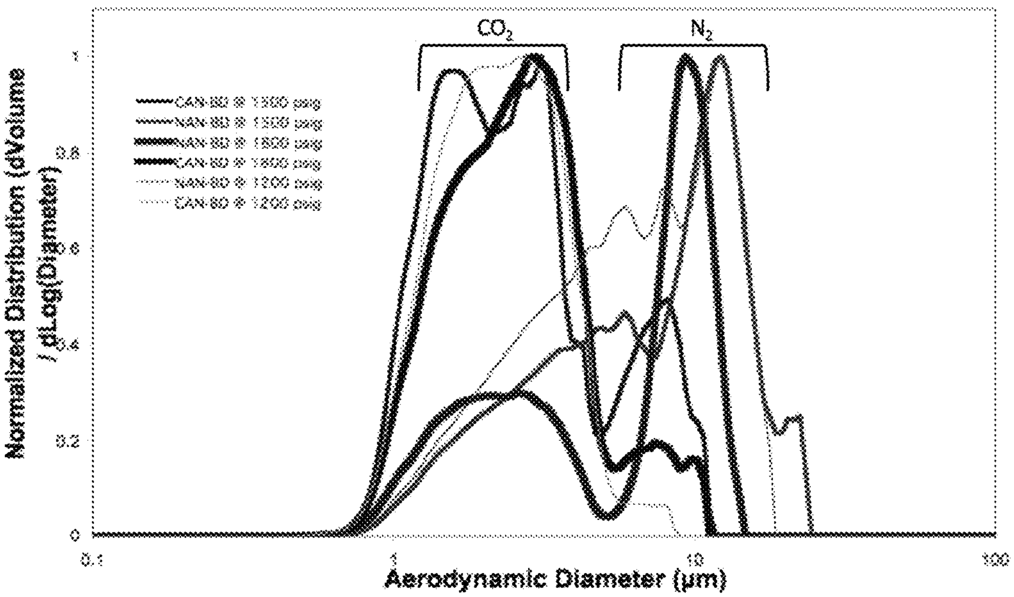
FIG. 6 shows a graph of the distribution of aerodynamic particle sizes produced from carbon dioxide ($CO_2$) nebulization and nitrogen ($N_2$) nebulization. The instrument employed in the measurement of the aerodynamic diameter (TSI Aerosizer DSP, Model 3225, equipped with an AeroDisperser, Model 3230) imparts a sufficient dispersing force to the powder that aerodynamic diameter can be considered roughly equivalent to the geometric diameter.
Figure 12:
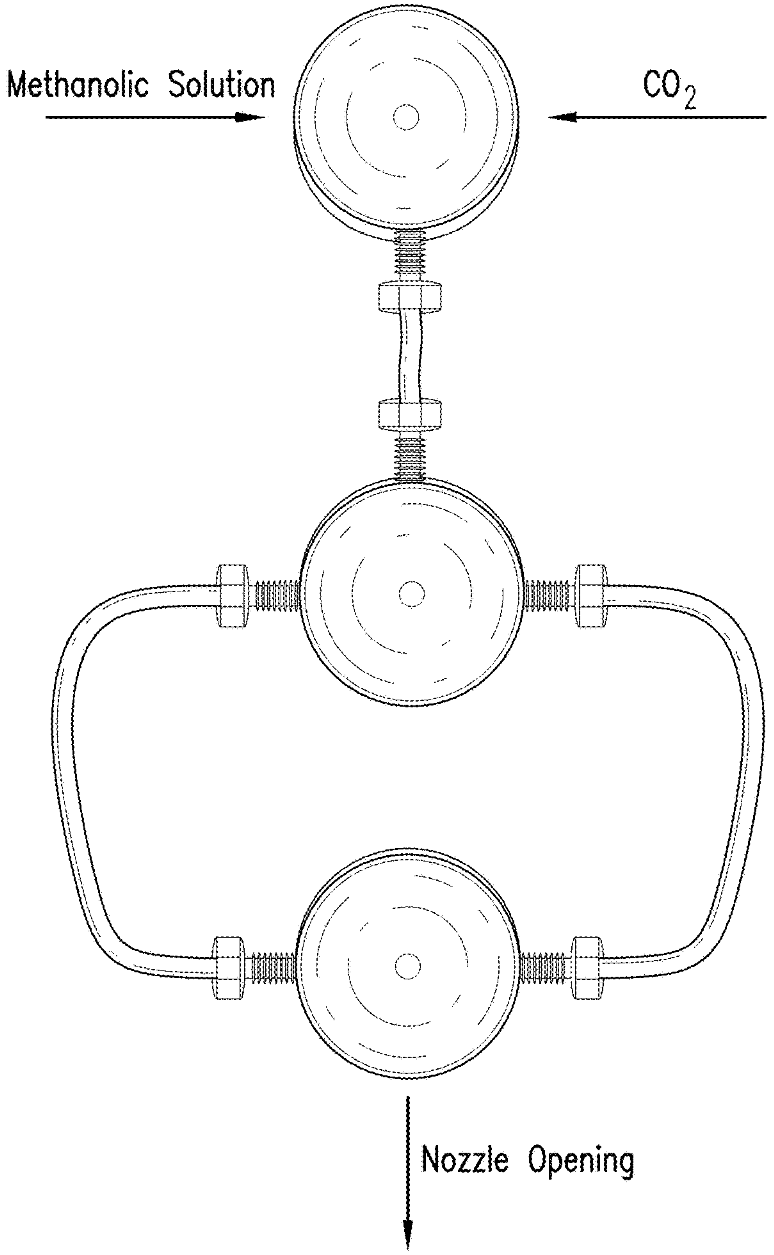
FIG. 12 shows a photograph of the nozzle of the invention as described in Example 2.

A methanol/water solution (7:3 methanol:water) comprising 16% w/w total dissolved solids was made. The dissolved solids were composed of 90% w/w mannitol and 10% methionine. The solution was divided in half and dried using the previously described CAN-BD process with the following parameters: 2.0 ml/min. carbon dioxide flow rate, 1.0 ml/min. solution flow rate, 40° C. nitrogen drying gas temperature, 40 L/min. nitrogen drying gas flow rate, 75 μm internal diameter fused silica restrictor, 5 cm long fused silica restrictor, and 0.45 μm Nylon powder-collection filter. One half of the solution was dried with the typical CAN-BD low-volume tee nozzle schematically depicted in FIG. 4, and the other half of the solution was dried with an improved nozzle design according to the invention, as shown in FIG. 12.

The dimensions of the improved nozzle in this example were as follows. The 0.35 mm original flowpath diameter expanded to 1.5 mm flowpath diameter, and then narrowed again to 0.35 mm flowpath diameter. The flowpath then bifurcated into two pathways of 1.5 mm diameter, then was again constrained to a final 0.35 mm diameter flowpath before exiting the nozzle.

Figure 13:
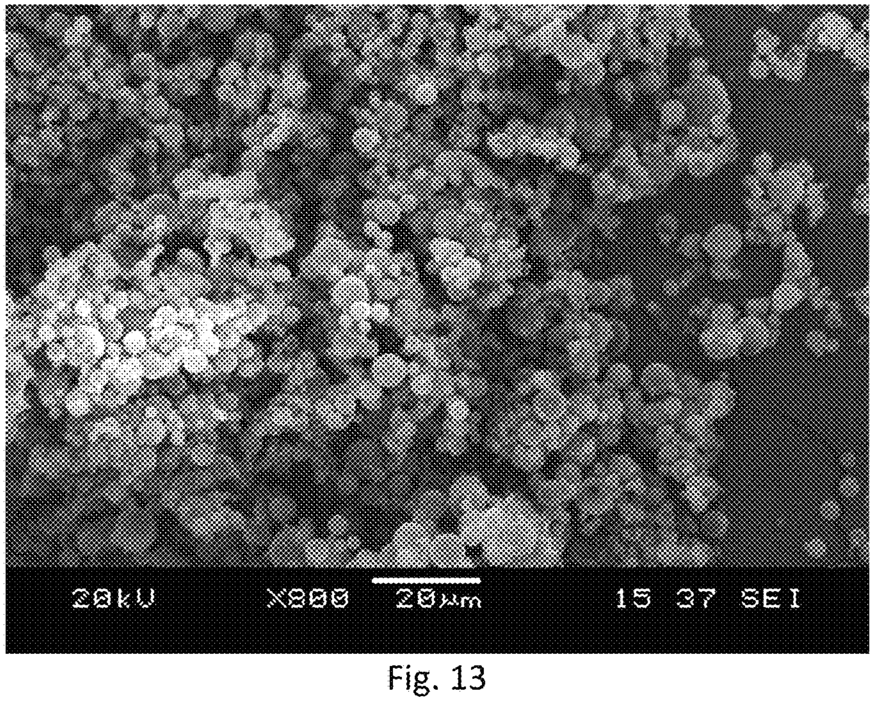
FIG. 13 shows an SEM of the 90% mannitol/10% methionine dry microparticulate powder produced by the CAN-BD nozzle described in U.S. Pat. No. 6,630,121 at 800× magnification.
Figure 14:
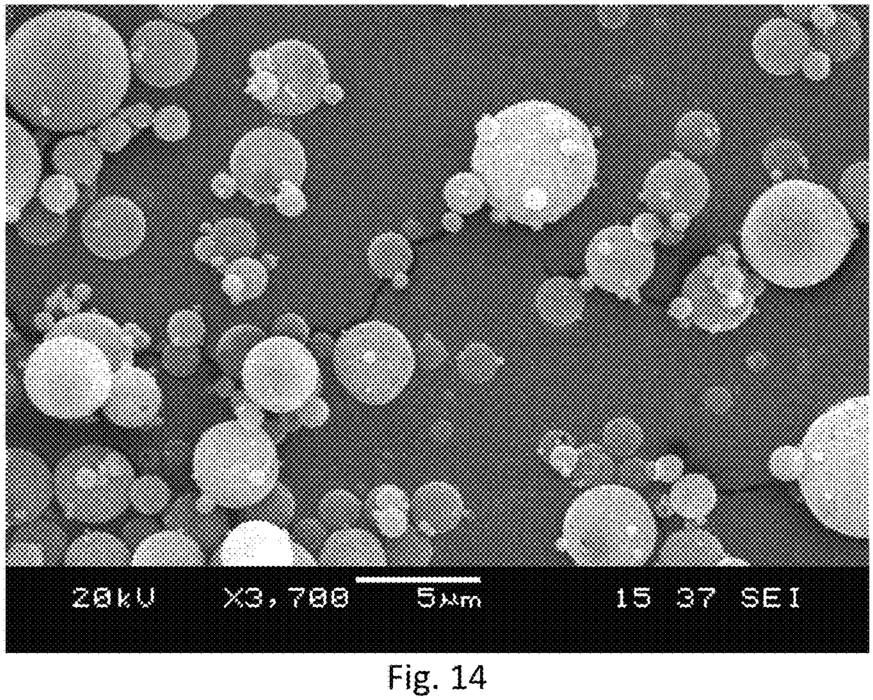
FIG. 14 shows an SEM of the 90% mannitol/10% methionine powder produced by the CAN-BD nozzle described in U.S. Pat. No. 6,630,121 at 3700× magnification.
Figure 15:
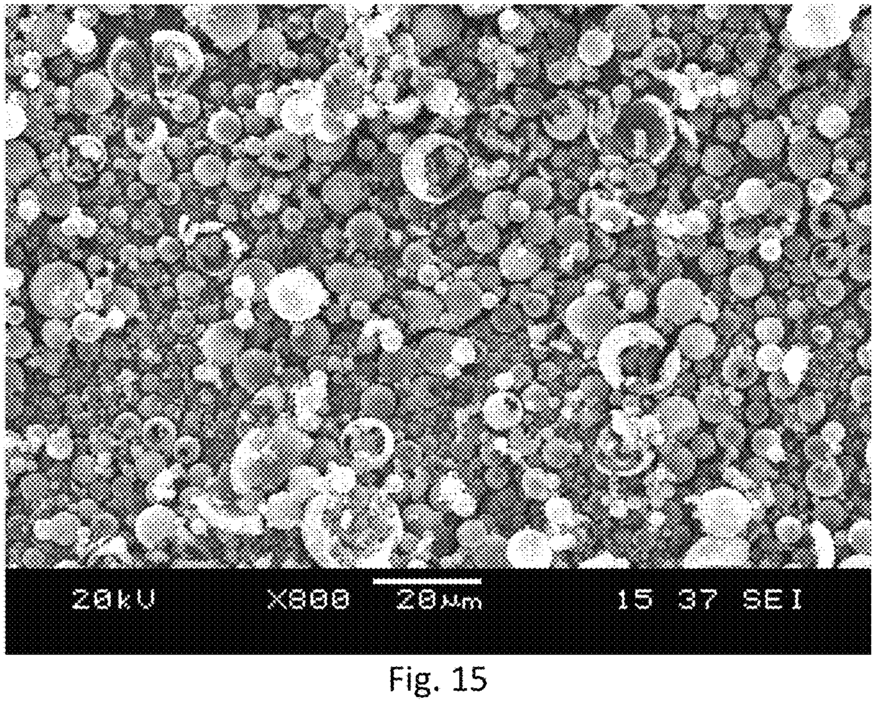
FIG. 15 shows an SEM of the 90% mannitol/10% methionine powder produced by the nozzle of the invention as described in Example 2, at 800× magnification.
Figure 16:
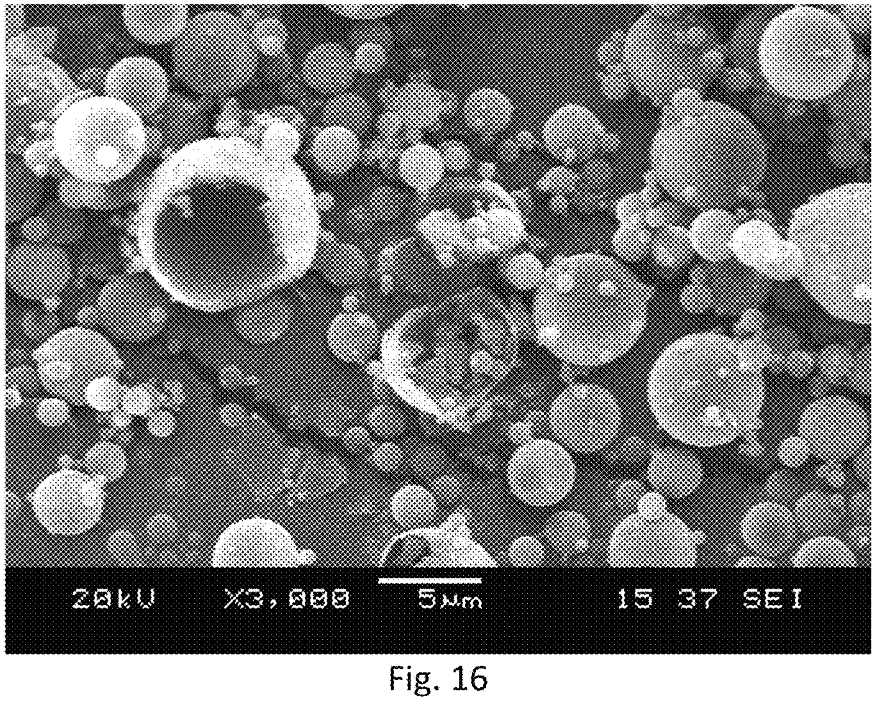
FIG. 16 shows an SEM of the 90% mannitol/10% methionine powder produced by the nozzle of the invention as described in Example 2, at 3000× magnification.

The resulting powder particles dried from the typical CAN-BD low-volume tee nozzle are shown in scanning electron micrographs (SEMs) in FIG. 13 and FIG. 14. The particles are predominantly solid spheres with occasional evidence of hollow particles scattered throughout the powder, as expected. The resulting powder particles dried from the improved nozzle according to the invention are shown in SEMs in FIG. 15 and FIG. 16. The powder particle distribution, although comprised of some solid spheres, contains significantly more (about 30%) hollow spheres as compared to the typical CAN-BD nozzle-prepared powder.

The specific embodiments and examples described in the present disclosure are illustrative only in nature and are not limiting of the invention defined by the following claims. Further aspects, embodiments and advantages of the methods of the present invention will be apparent in view of the present disclosure and are encompassed within the following claims.

REFERENCES

Ameri, M.; Maa, Y.-F. "Spray drying of biopharmaceuticals: stability and process considerations." *Dry. Technol.* 2006, 24, 763-768.

Baras, B.; Benoit, M.-A.; Gillard, J. "Parameters influencing the antigen release from spray-dried poly(D L-lactide) micro-particles." *Int. J. Pharm.* 2000, 200, 133-145.

Begat, P.; Price, R.; Harris, H.; Morton, D. A. V.; Staniforth, J. N. "The influence of force control agents on the cohesive-adhesive balance in dry powder inhaler formulations." *KONA*. 2005, 23, 109-121.

Bernstein, H.; Straub, J. A.; Brush, H. T.; Wing, R. E. *Microencapsulated Fluorinated Gases for Use as Imaging Agents*, Acusphere, Inc. USA U.S. Pat. No. 5,611,344, 1997.

Bittner, B.; Kissel, T. "Ultrasonic atomization for spray drying: a versatile technique for the preparation of protein loaded biodegradable microspheres." *J. Microencapsul.* 1999, 16, 325-341.

Cape, S. P.; Villa, J. A.; Huang, E. T. S.; Yang, T.-H.; Carpenter, J. F.; Sievers, R. E. "Preparation of active proteins, vaccines and pharmaceuticals as fine powders using supercritical or near-critical fluids." *Pharm. Res.* 2008, 25, 1967-1900.

Chew, N. Y. K.; Chan, H.-K. "Use of solid corrugated particles to enhance powder performance." *Pharm. Res.* 2001, 18, 1570-1577.

Freitas, S.; Merkle, H. P.; Gander, B. "Ultrasonic atomization into reduced pressure atmosphere: envisaging aseptic spray-drying for microencapsulation." *J. Control. Release.* 2004, 95, 185-195.

Fu, Y.-J.; Mi, F.-L.; Wong, T.-B.; Shyu, S.-S. "Characteristic and controlled release of anticancer drug loaded poly (D,L-lactide) microparticles prepared by spray drying technique." *J. Microencapsul.* 2001, 18, 733-747.

Geller, D. E.; Weers, J.; Heuerding, S. "Development of an inhaled dry-powder formulation of tobramycin using PulmoSphere™ technology." *J. Aerosol Med.* 2011, 24, 175-182.

Li, H.-Y.; Birchall, J. "Chitosan-modified dry powder formulations for pulmonary gene delivery." *Pharm. Res.* 2006, 23, 941-950.

Maa, Y.-F.; Costantino, H. R.; Nguyen, P.-A.; Hsu, C. C. "The effect of operating and formulation variables on the morphology of spray-dried particles." *Pharm. Dev. Technol.* 1997, 2, 213-223.

Maa, Y.-F.; Nguyen, P.-A. T.; Hsu, S. W. "Spray-drying of air-liquid interface sensitive recombinant human growth hormone." *J. Pharm. Sci.* 1998, 87, 152-159.

Masters, K. *Spray-drying: An Introduction to Principles, Operational Practice and Applications*. Leonard Hill, London, 1972.

Maury, M.; Murphy, K.; Kumar, S.; Maurer, A.; Lee, G. "Spray-drying of proteins: effects of sorbitol and trehalose on aggregation and FT-IR amide I spectrum of an immunoglobulin G." *Eur. J. Pharm. Biopharm.* 2005, 59, 251-261.

Mu, L.; Feng, S. S. "Fabrication, characterization and in vitro release of paclitaxel (taxol) loaded poly (lactic-co-glycolic acid) microspheres prepared by spray drying technique with lipid/cholesterol emulsifiers." *J. Control. Release.* 2001, 76, 239-254.

Narayan, P.; Marchant, D.; Wheatley, M. A. "Optimization of spray drying by factorial design for production of hollow microspheres for ultrasound imaging." *J. Biomed. Mater. Res.* 2001, 56, 333-341.

Sacchetti, M.; Van Oort, M. M. "Spray-drying and supercritical fluid particle generation techniques." In Hickey, A. J. (ed.) *Inhalation Aerosols, Physical and Biological Basis for Therapy, Vol.* 94, *Lung Biology in Health and Disease*. Marcel Dekker, New York, 1996. 337-384.

Samborska, K.; Witrowa-Rajchert, D.; Goncalves, A. "Spray-drying of alpha-amylase—the effect of process variables on the enzyme inactivation." *Dry. Technol.* 2005, 23, 941-953.

Sellers, S. P.; Clark, G. S.; Sievers, R. E.; Carpenter, J. F. "Dry powders of stable protein formulations from aqueous solutions prepared using supercritical $CO_2$-assisted aerosolization." *J. Pharm. Sci.* 2001, 90, 785-797.

Stahl, K.; Claesson, M.; Lilliehorn, P.; Linden, H.; Backstrom, K. "The effect of process variables on the degradation and physical properties of spray dried insulin intended for inhalation." *Int. J. Pharm.* 2002, 233, 227-237.

Straub, J.; Bernstein, H.; Chickering, D. E.; Randall, G. Porous Celecoxib Matrices and Methods of Manufacture Thereof, Acusphere, Inc. USA U.S. Pat. No. 6,589,557, 2003.

Ting, T.-Y.; Gonda, I.; Gipps, E. M. "Microparticles of polyvinyl alcohol for nasal delivery. I. Generation by spray-drying and spray-desolvation." *Pharm. Res.* 1992, 9, 1330-1335.

Vehring, R. "Pharmaceutical particle engineering via spray drying." *Pharm. Res.* 2008, 25, 999-1022.

Vehring, R.; Foss, W. R.; Lechuga-Ballesteros, D. "Particle formation in spray drying." *J. Aerosol Sci. Tech.* 2007, 38, 728-746.

Wang, F.-J.; Wang, C.-H. "Sustained release of etanidazole from spray dried microspheres prepared by non-halogenated solvents." *J. Control. Release.* 2002, 81, 263-280.

Zijlstra, G. S.; Hinrichs, W. L. J.; de Boer, A. H.; Frijlink, H. W. "The role of particle engineering in relation to formulation and de-agglomeration principle in the development of a dry powder formulation for inhalation of cetrorelix." *Eur. J. Pharm. Sci.* 2004, 23, 139-149.

What is claimed is:

1. A method of making a dry powder, comprising (a) delivering a liquid solution or suspension and an immiscible supercritical or near critical fluid to a flow path, (b) transporting a mixture of the liquid solution or suspension and the immiscible fluid along the flow path, wherein the flow path along which the mixture is transported includes two flow passages of different diameters, at least one flow divider which divides and diverts the flowing mixture into two separate passages, wherein the separate passages subsequently intersect to combine their respective flows into a single flowing stream, (c) rapidly reducing the pressure of the single flowing stream by passing the stream through a restrictor nozzle, whereby droplets are formed, and (d) passing the droplets through a flow of inert drying gas to form a dry powder.

2. The method of claim 1, wherein the flow path includes a first passage having a first diameter, followed by a second passage having a second diameter larger than the first diameter, followed by a third passage having a third diameter smaller than the second diameter, followed by the flow divider which divides and diverts the flowing mixture into two separate passages, wherein the separate passages subsequently intersect to combine their respective flows into a single flowing stream.

3. The method of claim 2, wherein the first diameter is in a range of from about 0.1 to about 3.0 mm, the second diameter is from about 0.01 to about 8 mm greater than the first diameter, and the third diameter is about 0.01 to about 8 mm less than the second diameter.

4. The method of claim 2, wherein the respective separate passages have diameters equal to the first diameter.

5. The method of claim 2, wherein the respective flows from the separate passages are combined into the single flowing stream in a fourth passage having a fourth diameter less than the diameters of the respective separate passages.

6. The method of claim 2, wherein the first diameter is in a range of from about 0.1 to about 3.0 mm, the second diameter is in a range of from about 1.0 to about 6 mm, the third diameter is in a range of from about 0.1 to about 3.0 mm, the respective separate passages have diameters in a range of from about 1.0 to about 3.0 mm, and the fourth diameter is in a range of from about 0.1 to about 3.0 mm.

7. The method of claim 1, wherein the flow divider divides and diverts the flowing mixture into, three or four separate passages which subsequently intersect to combine their respective flows into the single flowing stream.

8. The method of claim 1, wherein the separate passages have respective segments which are parallel to one another.

9. The method of claim 1, wherein the restrictor nozzle has a diameter of less than 0.1 mm.

10. The method of claim 1, wherein the supercritical or near critical fluid is carbon dioxide.

11. The method of claim 1, wherein the liquid solution or suspension comprises at least one active ingredient.

12. The method of claim 11, wherein the active ingredient is at least one selected from the group consisting of vaccine, insulin, amino acid, peptide, protein, enzyme, anti-viral, anti-fungal, antibiotic, anti-inflammatory agent, antihistamine, analgesic, anti-cancer agent, antimicrobial agent, immune suppressant, thrombolytic, anticoagulant, central nervous system stimulant, decongestant, diuretic vasodilator, antipsychotic, neurotransmitter, sedative, hormone, anesthetic, and siRNA.

13. The method of claim 1, wherein the dry powder comprises at least 30% of particles of a size of less than 5.8 μm as modeled by an Andersen Cascade Impactor according to US Pharmacopeia <601>.

14. The method of claim 1, wherein the inert drying gas is nitrogen or carbon dioxide.

15. The method of claim 1, wherein the method is conducted at a temperature of not more than 40° C.

16. The method of claim 2, wherein the supercritical or near critical fluid is carbon dioxide.

17. The method of claim 2, wherein the liquid solution or suspension comprises at least one active ingredient.

18. The method of claim 17, wherein the active ingredient is at least one selected from the group consisting of vaccine, insulin, amino acid, peptide, protein, enzyme, anti-viral, anti-fungal, antibiotic, anti-inflammatory agent, antihistamine, analgesic, anti-cancer agent, antimicrobial agent, immune suppressant, thrombolytic, anticoagulant, central nervous system stimulant, decongestant, diuretic vasodilator, antipsychotic, neurotransmitter, sedative, hormone, anesthetic, and siRNA.

19. The method of claim 2, wherein the dry powder comprises at least 30% of particles of a size of less than 5.8 μm as modeled by an Andersen Cascade Impactor according to US Pharmacopeia <601>.

20. The method of claim 2, wherein the inert drying gas is nitrogen or carbon dioxide.

21. The method of claim 2, wherein the method is conducted at a temperature of not more than 40° C.

* * * * *